United States Patent
Chen et al.

(10) Patent No.: US 11,839,456 B2
(45) Date of Patent: Dec. 12, 2023

(54) METHOD FOR DETERMINING MAXIMUM VALUE OF HEART RATE DATA OF USER PEFFORMING PHYSICAL ACTIVITY

(71) Applicant: bOMDIC, Inc., New Taipei (TW)

(72) Inventors: Szu-Hong Chen, New Taipei (TW); Pin-Yu Chen, New Taipei (TW); Tai-Yu Huang, New Taipei (TW); Yu-Ting Liu, New Taipei (TW)

(73) Assignee: BOMDIC INC., New Taipei (TW)

( * ) Notice: Subject to any disclaimer, the term of this patent is extended or adjusted under 35 U.S.C. 154(b) by 212 days.

(21) Appl. No.: 17/376,146

(22) Filed: Jul. 14, 2021

(65) Prior Publication Data

US 2023/0023736 A1    Jan. 26, 2023

(51) Int. Cl.
| | |
|---|---|
| A61B 5/24 | (2021.01) |
| A61B 5/024 | (2006.01) |
| A61B 5/11 | (2006.01) |
| A61B 5/083 | (2006.01) |
| A61B 5/0205 | (2006.01) |

(52) U.S. Cl.
CPC ........ A61B 5/02438 (2013.01); A61B 5/0205 (2013.01); A61B 5/0833 (2013.01); A61B 5/1118 (2013.01); *A61B 2562/0219* (2013.01)

(58) Field of Classification Search
CPC . A61B 5/02438; A61B 5/0205; A61B 5/0833; A61B 5/1118; A61B 2562/0219
USPC .......................................................... 600/508
See application file for complete search history.

(56) References Cited

U.S. PATENT DOCUMENTS

| | | | | |
|---|---|---|---|---|
| 9,517,028 | B1* | 12/2016 | Saalasti | A61B 5/486 |
| 9,848,823 | B2* | 12/2017 | Raghuram | A61B 5/7246 |
| 10,524,670 | B2* | 1/2020 | Raghuram | A61B 5/02438 |
| 2016/0058356 | A1* | 3/2016 | Raghuram | A61B 5/222 |
| | | | | 600/483 |
| 2016/0374569 | A1* | 12/2016 | Breslow | A61B 5/1112 |
| | | | | 600/301 |
| 2017/0049334 | A1* | 2/2017 | Saalasti | A61B 5/222 |
| 2017/0105664 | A1* | 4/2017 | Olivier | A61B 5/14551 |
| 2017/0216672 | A1* | 8/2017 | Wisbey | H04R 1/1041 |
| 2017/0316425 | A1* | 11/2017 | Ackland | G16H 50/20 |
| 2019/0110755 | A1* | 4/2019 | Capodilupo | A61B 5/02416 |

* cited by examiner

*Primary Examiner* — Carl H Layno
*Assistant Examiner* — Michael J Lau
(74) *Attorney, Agent, or Firm* — Chieh-Mei Wang (57) ABSTRACT

The present invention discloses a method for determining a maximum value of a heart rate data of a user performing a physical activity. Acquire first heart rate data in a first duration of the physical activity performed by the user. Acquire motion data in the first duration of the physical activity performed by the user. Calculate second heart rate data based on the motion data in the first duration of the physical activity performed by the user by a mathematical model and estimate the maximum value of the heart rate data of the user based on a comparison between the first first heart rate data and the second heart rate data.

15 Claims, 6 Drawing Sheets

METHOD FOR DETERMINING MAXIMUM VALUE OF HEART RATE DATA OF USER PEFFORMING PHYSICAL ACTIVITY

BACKGROUND OF THE INVENTION

1. Field of the Invention

The present invention relates to a method for monitoring the cardiac capacity of the user, and more particularly to a method for determining the maximum value of the heart rate data of the user performing the physical activity.

2. Description of Related Art

The maximum value of the heart rate data of the user may mean the cardiac capacity of the user. Take the maximum heart rate for example in the following description.

The maximum heart rate (its unit may be beats per minute (BPM)) represents the highest heart rate the user can achieve through the physical effort. The maximum heart rate may be used to calculate other exercise parameter, such as the fitness level and the energy expenditure, or to create appropriate heart rate zones for the user.

The most direct way to determine the maximum heart rate is measuring the user's highest heart rate when the user performs the maximal exercise. However, the user may not want to perform the maximal exercise because of fatigue or injury. Besides, it is unsafe for seniors or patients to perform the maximal exercise.

There are many methods for estimating the maximum heart rate. These methods may be associated with age, gender, activity level or weight. For example, the maximum heart rate is equal to 220 minus age (unit: beats per minute (BPM)). Most of these methods may produce a larger error. Once there is an error X1 in the maximum heart rate, the exercise parameter calculated based on the maximum heart rate may have an error X2 more than the error X1.

Many methods are only able to update the maximal heart rate value upwards. In other words, the maximal heart rate increases with time. However, the maximal heart rate may decrease with time (e.g., age).

Accordingly, the present invention proposes a method for determining the maximum value of the heart rate data (e.g., maximum heart rate) of the user performing the physical activity to overcome the above-mentioned disadvantages.

SUMMARY OF THE INVENTION

Each of the first heart rate data and the motion data is acquired in a first duration of the physical activity performed by the user by a respective sensor. The present invention uses a major mathematical relationship (determined based on a major physiological mechanism of a human body) which can calculate the second heart rate data based on the motion data. The calculated second heart rate data is also constrained by the maximum value of the heart rate data defined in the major mathematical relationship. Further, a plurality of candidates of the maximum value of the heart rate data is provided and each candidate of the maximum value of the heart rate data is defined in the corresponding major mathematical relationship. For each of the candidates of the maximum value of the heart rate data, it has a difference that the calculated second heart rate data constrained by the candidate of the maximum value of the heart rate data varies with the external workload with the motion data or time in the corresponding major mathematical relationship. For each of the candidates of the maximum value of the heart rate data, a comparison (e.g., the minimum difference) between the first heart rate data and the corresponding second heart rate data calculated based on the difference is made to be used to choose one of the candidates of the maximum value of the heart rate data as an estimation of the maximum value of the heart rate data of the user. In other words, the user having the maximum value of the heart rate data being the candidate of the maximum value of the heart rate data corresponding to the comparison (e.g., the minimum difference) between the first heart rate data and the second heart rate data has a largest probability of having the first heart rate data and the motion data acquired in the first duration of the physical activity; therefore, a comparison (e.g., the minimum difference) between the first heart rate data and the corresponding second heart rate data calculated based on the difference made for each of the candidates of the maximum value of the heart rate data can increase an precision of the estimation of the maximum value of the heart rate data of the user.

By the algorithm implemented in the computer of the present invention, the computer of the present invention performs operations described in claims or the following descriptions to determine the maximum value of the heart rate data of the user performing the physical activity.

In one embodiment, the present invention discloses a method for determining a maximum value of a heart rate data of a user performing a physical activity. The method comprises: acquiring, by a heart rate sensor, first heart rate data in a first duration of the physical activity performed by the user; acquiring, by a motion sensor, motion data in the first duration of the physical activity performed by the user; providing a plurality of candidates of the maximum value of the heart rate data; for each first candidate of the plurality of candidates of the maximum value of the heart rate data, performing, by a processor, a process comprising steps of: calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by the first candidate of the maximum value of the heart rate data defined in the major mathematical relationship (or constrained by a minimum value of the heart rate data and the first candidate of the maximum value of the heart rate data defined in the major mathematical relationship); and making a comparison between the first heart rate data and the second heart rate data; and choosing, by the processor, one first candidate of the plurality of candidates of the maximum value of the heart rate data as an estimation of the maximum value of the heart rate data of the user based on each comparison between the first heart rate data and the second heart rate data.

In one embodiment, the present invention discloses a method for determining a maximum value of a heart rate data of a user performing a physical activity. The method comprises: acquiring, by a heart rate sensor, first heart rate data in a first duration of the physical activity performed by the user; acquiring, by a motion sensor, motion data in the first duration of the physical activity performed by the user; providing a plurality of candidates of the maximum value of the heart rate data; for each first candidate of the plurality of candidates of the maximum value of the heart rate data, performing, by a processor, a process comprising steps of: calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by a minimum value of the heart rate data and the first candidate of the maximum value of the heart rate data defined in the major mathematical relationship; and making a comparison between the first heart rate data and the second heart rate data; and choosing, by the processor, one first candidate of the plurality of candidates of the maximum value of the heart rate data as an estimation of the maximum value of the heart rate data of the user based on each comparison between the first heart rate data and the second heart rate data; wherein the major mathematical relationship comprises a first minor mathematical relationship between the motion data and a first portion of the second heart rate data and a second minor mathematical relationship between the motion data and a second portion of the second heart rate data, wherein the first minor mathematical relationship is determined based on a first minor physiological mechanism of the major physiological mechanism of the human body and the second minor mathematical relationship is determined based on a second minor physiological mechanism of the major physiological mechanism of the human body, wherein a first response speed of the first portion of the second heart rate data in the first minor mathematical relationship is more than a second response speed of the second portion of the second heart rate data in the second minor mathematical relationship if the same activity intensity is applied in the first minor mathematical relationship and the second minor mathematical relationship.

In one embodiment, the present invention discloses a method for determining a maximum value of a heart rate data of a user performing a physical activity. The method comprises: acquiring, by a heart rate sensor, first heart rate data in a first duration of the physical activity performed by the user; acquiring, by a motion sensor, motion data in the first duration of the physical activity performed by the user; providing a plurality of candidates of the maximum value of the heart rate data; for each first candidate of the plurality of candidates of the maximum value of the heart rate data, performing, by a processor, a process comprising steps of: calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by a minimum value of the heart rate data and the first candidate of the maximum value of the heart rate data defined in the major mathematical relationship; and making a comparison between the first heart rate data and the second heart rate data; and choosing, by the processor, one first candidate of the plurality of candidates of the maximum value of the heart rate data as an estimation of the maximum value of the heart rate data of the user based on each comparison between the first heart rate data and the second heart rate data; wherein the major mathematical relationship comprises a first minor mathematical relationship between the motion data and a first portion of the second heart rate data and a second minor mathematical relationship between the motion data and a second portion of the second heart rate data, wherein the first minor mathematical relationship is determined based on a first minor physiological mechanism of the major physiological mechanism of the human body and the second minor mathematical relationship is determined based on a second minor physiological mechanism of the major physiological mechanism of the human body, wherein a first threshold of an activity intensity above which the first minor mathematical relationship is operated is less than a second threshold of the activity intensity above which the second minor mathematical relationship is operated.

The detailed technology and above preferred embodiments implemented for the present invention are described in the following paragraphs accompanying the appended drawings for people skilled in the art to well appreciate the features of the claimed invention.

BRIEF DESCRIPTION OF THE DRAWINGS

The foregoing aspects and many of the accompanying advantages of this invention will become more readily appreciated as the same becomes better understood by reference to the following detailed description when taken in conjunction with the accompanying drawings, wherein.

DETAILED DESCRIPTION OF THE ILLUSTRATED EMBODIMENTS

The detailed explanation of the present invention is described as following. The described preferred embodiments are presented for purposes of illustrations and description and they are not intended to limit the scope of the present invention.

The physiological mechanism in each of Physiological Phenomenon, Example I and Example II in the following description may be regarded as a major physiological mechanism or a minor physiological mechanism.

Physiological Phenomenon

Physiologically, the receptors associated with the physiological mechanism of the human body receives the external workload in demand and transmits the message with the external workload in demand to the central nervous system of the human body; then, the central nervous system of the human body can adjust the heart activity (e.g., the heart rate) to meet the external workload in demand. Further, the receptors associated with the physiological mechanism of the human body receives the external workload in demand based on a physiological parameter associated with (e.g., required in) the physiological mechanism and transmits the message with the external workload in demand to the central nervous system of the human body; then, the central nervous system of the human body can adjust the heart activity (e.g., the heart rate) to meet the external workload in demand.

Example I (of Physiological Phenomenon)

Take the physiological mechanism being an aerobic glycolysis for ATP production in the active muscle, the physiological parameter associated with the physiological mechanism being the oxygen supply in the aerobic glycolysis for ATP production in the active muscle and the external workload being a power/speed for example; when the aerobic glycolysis for ATP production in the active muscle happens, the receptors associated with the aerobic glycolysis receives the power/speed (e.g., external workload) in demand based on the oxygen supply associated with (e.g., required in) the aerobic glycolysis for ATP production in the active muscle, the central nervous system of the human body can adjust the heart activity (e.g., the heart rate) to meet the power/speed (e.g., external workload) in demand; however, the present invention is not limited to this case.

Example II (of Physiological Phenomenon)

Take the physiological mechanism being an aerobic removal of lactate in the whole body, the physiological parameter associated with the physiological mechanism being the oxygen supply in aerobic removal of lactate in the whole body and the external workload being a power/speed for example; when aerobic removal of lactate in the whole body happens, the receptors associated with aerobic removal of lactate receives the power/speed (e.g., external workload) in demand based on the oxygen supply associated with (e.g., required in) aerobic removal of lactate in the whole body, the central nervous system of the human body can adjust the heart activity (e.g., the heart rate) to meet the power/speed (e.g., external workload) in demand; however, the present invention is not limited to this case.

Activity Intensity

The activity intensity may refer to how much energy is expended when taking activity. The activity intensity may define how hard the body has to work to overcome an activity/exercise. The activity intensity may be measured in the form of the internal workload. The parameter of the activity intensity associated with the internal workload may be associated with a heart rate, an oxygen consumption, a pulse, a respiration rate and RPE (rating perceived exertion). The activity intensity may be measured in the form of the external workload. The parameter of the activity intensity associated with the external workload may be associated with a speed, an acceleration, a power, a force, an energy expenditure rate, a motion intensity, a motion cadence or other kinetic data created by the external workload resulting in energy expenditure. The heart rate may be often used as a parameter of the activity intensity.

Figure 1:
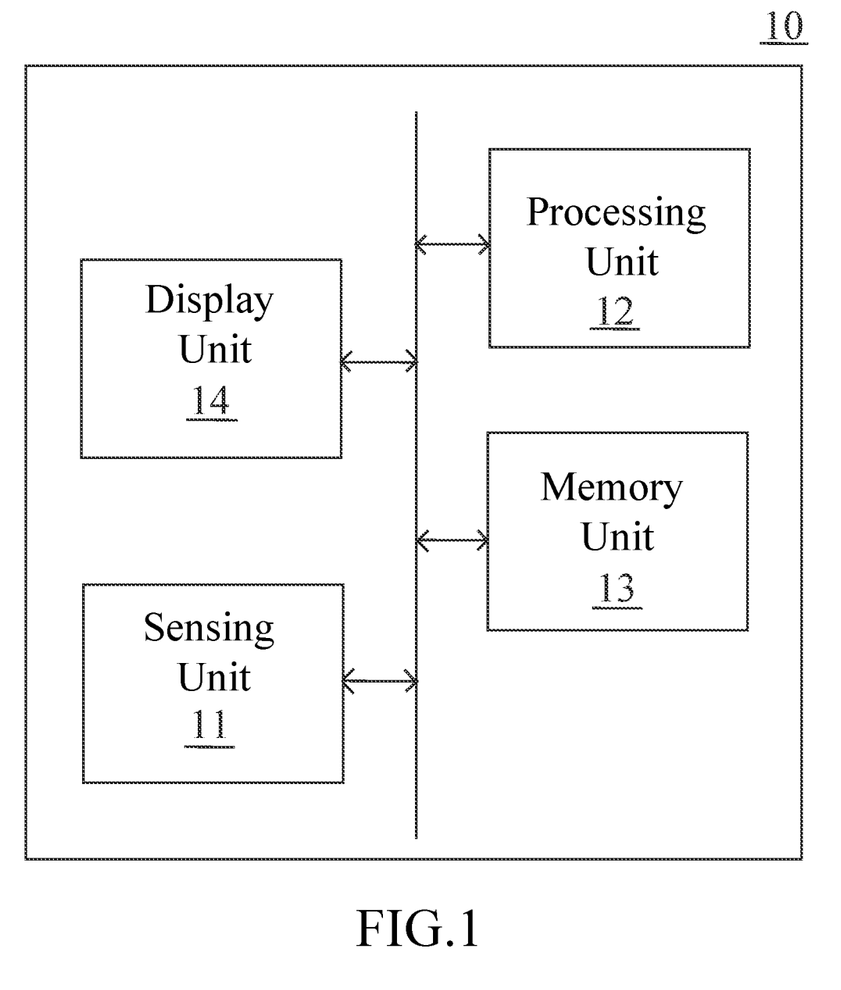
FIG. 1 illustrates a schematic block diagram of an exemplary apparatus in the present invention.

The method in the present invention may be applied in all kinds of apparatuses, such as a measurement system, the device worn on the individual (e.g., the device attached to the wrist belt or chest belt), a wrist top device, a mobile device, a portable device, a personal computer, a server or a combination thereof. FIG. 1 illustrates a schematic block diagram of an exemplary apparatus 10 in the present invention. The apparatus 10 may comprise a sensing unit 11 (e.g., at least one sensor), a processing unit 12, a memory unit 13 and a displaying unit 14. One unit may communicate with another unit in a wired or wireless way. The apparatus 10 may comprise at least one device; the sensing unit 11 may be in one device (e.g., the device worn on the individual or watch) and the processing unit 12 may be in another device (e.g., mobile device or mobile phone); the sensing unit 11 and the processing unit 12 may be in a single device (e.g., the device worn on the individual or watch). The sensing unit 11 may be attached to/comprised in a belt worn on the individual. The sensing unit 11 may be a sensor (e.g., heart rate sensor) which may measure a signal associated with the physiological data, the cardiovascular data or the internal workload from the person's body. The signal may be measured by applying a skin contact from chest, wrist or any other human part. The sensing unit 11 may comprise a second sensor (e.g., motion sensor) which may measure the activity/exercise intensity associated with the external workload. The second sensor may comprise at least one of an accelerometer, a magnetometer and a gyroscope. The sensing unit 11 may further comprise a position sensor (e.g., GPS: Global Positioning System). The sensing unit 11 may comprises at least two sensors described above. The processing unit 12 may be any suitable processing device for executing software instructions, such as a central processing unit (CPU). The processing unit 12 may be a computing unit. The apparatus 10 may comprise at least one device; a first portion of the computing unit may be in one device (e.g., the device worn on the individual or watch), a second portion of the computing unit may be in another device (e.g., mobile device or mobile phone) and a first portion of the computing unit may communicate with a second portion of the computing unit in a wired or wireless way; a first portion of the computing unit and a second portion of the computing unit may be in a single device (e.g., the device worn on the individual or watch). The memory unit 13 may include random access memory (RAM) and read only memory (ROM), but it is not limited to this case. The memory unit 13 may include any suitable non-transitory computer readable medium, such as ROM CD-ROM, DVD-ROM and so on. Also, the non-transitory computer readable medium is a tangible medium. The non-transitory computer readable medium includes a computer program code which, when executed by the processing unit 12, causes the apparatus 10 to perform desired operations (e.g., operations listed in claims). The display unit 14 may be a display for displaying an estimation of the maximum value of the heart rate data, the related exercise parameter (e.g., the fitness level of the user, energy expenditure, or to create appropriate heart rate zones for the user) and the related exercise guiding/exercise scheme. The displaying mode may be in the form of words, a voice or an image. The sensing unit 11, the processing unit 12, the memory unit 13 and the displaying unit 14 in the apparatus 10 may have any suitable configuration and it doesn't be described in detail therein.

Figure 2:
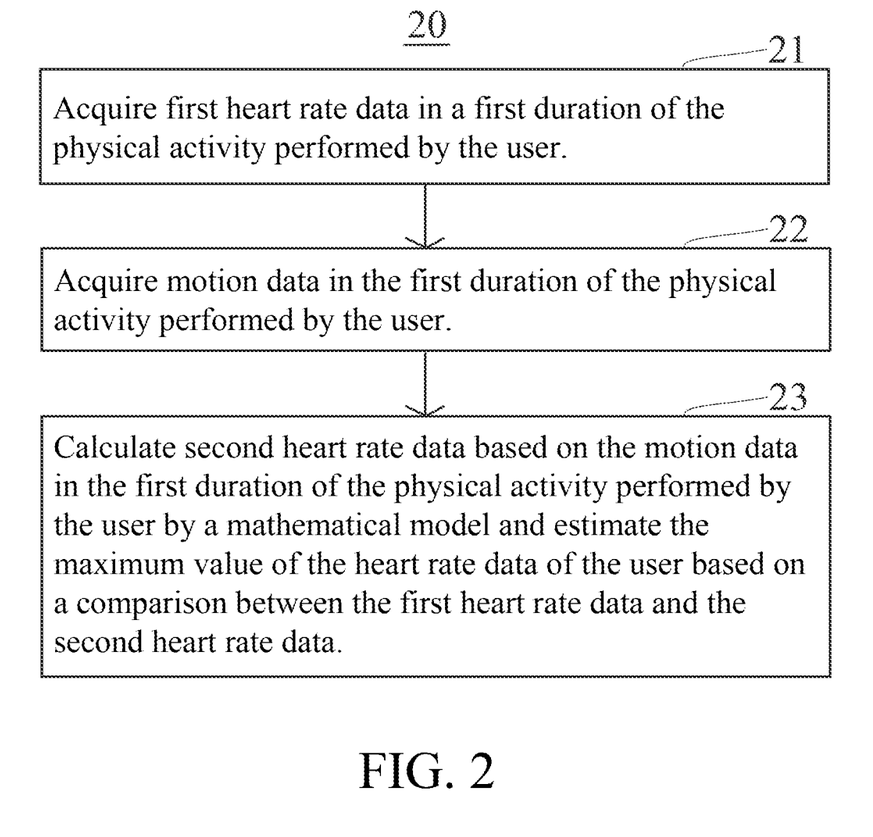
FIG. 2 illustrates a method for determining a maximum value of a heart rate data of a user performing a physical activity.

FIG. 2 illustrates a method 20 for determining a maximum value of a heart rate data of a user performing a physical activity. The physical activity may be an activity with a lower exertion or an exercise. The method comprises:

Step 21: acquire first heart rate data in a first duration of the physical activity performed by the user (by a heart rate sensor);

Step 22: acquire motion data in the first duration of the physical activity performed by the user (by a motion sensor); and Step 23: calculate second heart rate data based on the motion data in the first duration of the physical activity performed by the user by a mathematical model and estimate the maximum value of the heart rate data of the user based on a comparison between the first heart rate data and the second heart rate data.

The parameter of the first heart rate data acquired in step 21 may be a heart rate data. The heart rate data may be a heart rate, a pulse rate, a parameter determined based on the ECG/PPG signal or any other suitable parameter. For convenience of description, the parameter of the first heart rate data is a heart rate; however, the present invention is not limited to this case. The parameter of the motion data acquired in step 22 may be a motion parameter. The motion parameter may be a speed, an acceleration, a power, a force, an energy expenditure rate, a motion intensity, a motion cadence or a body movement. For convenience of description, the parameter of the motion data is a power/speed; however, the present invention is not limited to this case. Each of the first heart rate data and the motion data is acquired in a first duration of the physical activity performed by the user by a respective sensor.

Step 23 will be described in detail hereafter.

Figure 3:
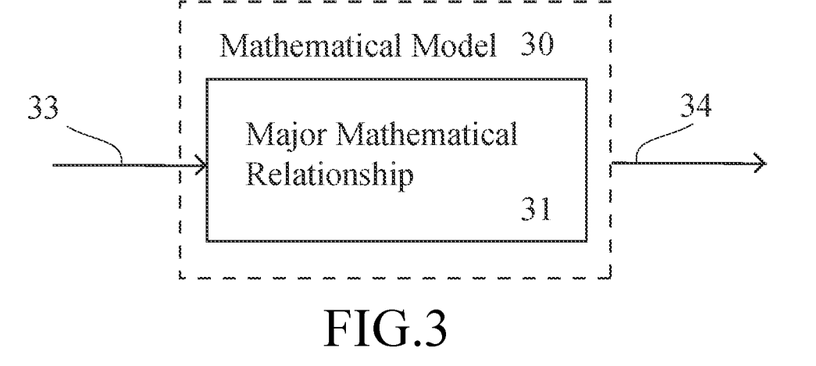
FIG. 3 illustrates the mathematical model in the step 23 in FIG. 2.

FIG. 3 illustrates the mathematical model 30 in the step 23 in FIG. 2. The mathematical model 30 may comprise a major mathematical relationship 31 between the motion data 33 and the second heart rate data 34. The major mathematical relationship 31 in the mathematical model 30 may be determined based on a major physiological mechanism of the human body. By the major mathematical relationship 31 in the mathematical model 30, the second heart rate data 34 can be calculated based on the motion data 33 in the first duration of the physical activity performed by the user. If the external workload with the motion data 33 is maintained, the second heart rate data 34 may increase as the time increases. When the time approaches infinity, the second heart rate data 34 may by a constant (see the curve 43 in FIG. 6). The calculated second heart rate data 34 in the first duration of the physical activity will be compared to the first heart rate data 32 acquired by the heart rate sensor in the first duration of the physical activity, which will be described in detail hereafter (see FIG. 4). The parameter of the second heart rate data acquired in step 23 may be a heart rate data. The heart rate data may be a heart rate, a pulse rate, a parameter determined based on the ECG/PPG signal or any other suitable parameter. For convenience of description, the parameter of the second heart rate data is a heart rate; however, the present invention is not limited to this case.

The major mathematical relationship 31 in the mathematical model 30 determined based on the major physiological mechanism of the human body also defines a minimum value of the heart rate data and a maximum value of the heart rate data. In one embodiment, the calculated second heart rate data 34 can be constrained by the maximum value of the heart rate data when the user performs the physical activity with the varying activity intensity in the form of the external workload. In another embodiment, the calculated second heart rate data 34 can be constrained by the minimum value (e.g., resting heart rate if the parameter of the second heart rate data is a heart rate) of the heart rate data and the maximum value of the heart rate data when the user performs the physical activity with the varying activity intensity in the form of the external workload. For example, the minimum value of the heart rate data and the maximum value of the heart rate data are respectively the heart rate of 80 BPM and the heart rate of 200 BPM defined in the major mathematical relationship 31 and then the calculated second heart rate data 34 is the heart rate of at least 80 BPM and at most 200 BPM. For example, the minimum value of the heart rate data and the maximum value of the heart rate data are respectively the heart rate reserve (HRR: The percentage of the heart rate reserve represents the ratio of the difference between the heart rate and the resting heart rate to the difference between the maximum heart rate and the resting heart rate) of 0 and the heart rate reserve of 1 defined in the major mathematical relationship 31 and then the calculated second heart rate data 34 is the heart rate reserve of at least 0 and at most 1. The minimum value of the heart rate data may be fixed or not fixed. The maximum value of the heart rate data of the user may mean the cardiac capacity of the user. The maximum value of the heart rate data of the user performing the physical activity always varies with the physical effort resulting from the physical activity. The maximum value of the heart rate data of the user may be used to calculate other exercise parameter which may be displayed on the wearable device to inform the user of the message associated with exercise, health, fitness or wellness. The maximum value of the heart rate data may be determined at an optimized frequency or in real time for subsequent application. The heart rate data of the user used for estimating its maximum value may be a heart rate, a pulse rate, a parameter determined based on the ECG/PPG signal or any other suitable parameter. For convenience of description, the heart rate data of the user used for estimating its maximum value is a heart rate; however, the present invention is not limited to this case.

Figure 4:
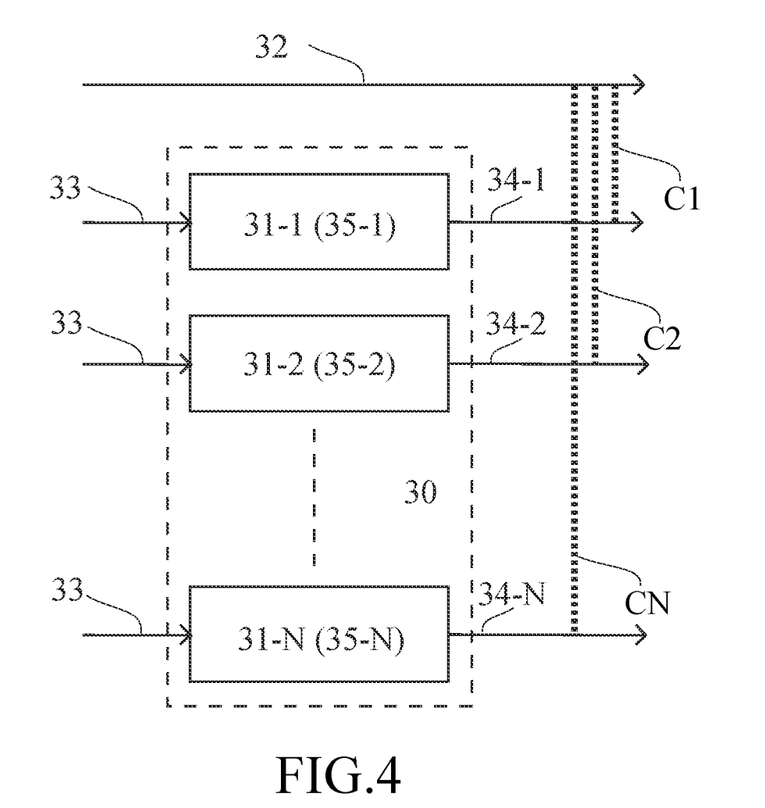
FIG. 4 specifically illustrates the step 23 in FIG. 2.

FIG. 4 specifically illustrates the step 23 in FIG. 2. In order to determining the maximum value of the heart rate data of the user performing the physical activity (e.g., at an optimized frequency or in real time), a plurality of candidates of the maximum value of the heart rate data 35-1, 35-2, . . . , 35-N are provided and each major mathematical relationship 31-$i$ (i=1~N) has a corresponding candidate of the maximum value of the heart rate data 35-$i$ (i=1~N); for each of the candidates of the maximum value of the heart rate data 35-1, 35-2, . . . , 35-N, calculate the second heart rate data 34-1, 34-2, . . . , 34-N based on the motion data 33 in the first duration of the physical activity by the major mathematical relationship 31-1, 31-2, . . . , 31-N in the mathematical model 30 and make a comparison C1, C2, . . . , CN between the first heart rate data 32 and the second heart rate data 34-1, 34-2, . . . , 34-N; finally, choose one of the candidates of the maximum value of the heart rate data 35-1, 35-2, . . . , 35-N of the user as an estimation of the maximum value of the heart rate data based on each comparison C1, C2, . . . , CN between the first heart rate data 32 and the second heart rate data 34-1, 34-2, . . . , 34-N. The candidate with the minimum difference between the first heart rate data 32 and the second heart rate data 34-1, 34-2, . . . , 34-N may be chosen as an estimation of the maximum value of the heart rate data. In one embodiment, the candidate with the minimum difference (e.g., Mean Absolute Error (MAE) or the minimum of the ratio of the integrated data-difference in the duration T to the duration T;

the data-difference may have any suitable form, such as the absolute value of the data-difference or the square of the data-difference) in the comparison between the first heart rate data 32 and the second heart rate data 34-1, 34-2, . . . , 34-N in the first duration may be chosen as an estimation of the maximum value of the heart rate data; however, the present invention is not limited to this case.

Take the following case in Table 1 for example. In this example, for convenience of description, suppose that the first duration is extremely short such that motion data 33 only has the speed of 6 km/hr and, correspondingly, the first heart rate data 32 only has the heart rate of 150 BPM in the first duration. However, the present invention is not limited to this case; for example, the motion data 33 of the speed varying with time and the first heart rate data of the heart rate varying with time are measured in the first duration.

the second heart rate data 34; (C1) the second heart rate data 34 of the heart activity is generated to meet (B1) the motion data 33 of the external workload determined based on (A1) the value of the physiological parameter associated with the major physiological mechanism of the human body. The physiological parameter associated with the major physiological mechanism of the human body may result from a physiological requirement in the major physiological mechanism of the human body. The physiological parameter associated with the major physiological mechanism of the human body may be the physiological parameter required in the major physiological mechanism of the human body; for example, the physiological parameter associated with the major physiological mechanism of the human body may be an oxygen supply in Example I and Example II; however, the present invention is not limited to this case.

TABLE 1

| motion data (speed) | first heart activity data (heart rate) | the candidate of the maximum value of the heart activity parameter defined in the major mathematical relationship (heart rate) | second heart activity data (heart rate) | the absolute value of the difference between the first heart activity data and the second heart activity data (heart rate) | an estimation of the maximum value of the heart activity parameter (heart rate) |
|---|---|---|---|---|---|
| 6 km/hr | 150 BPM | 185 BPM | 136 BPM | 14 BPM | 195 BPM |
| 6 km/hr | 150 BPM | 190 BPM | 145 BPM | 5 BPM | |
| 6 km/hr | 150 BPM | 195 BPM | 151 BPM | 1 BPM | |
| 6 km/hr | 150 BPM | 200 BPM | 158 BPM | 8 BPM | |

How to determine the major mathematical relationship in the mathematical model based on a major physiological mechanism of a human body:

It should be noticed that the major physiological mechanism may be divided into (or comprise) a plurality of minor physiological mechanisms or may not be divided into a plurality of minor physiological mechanisms. If the major physiological mechanism may not be divided into a plurality of minor physiological mechanisms, the major physiological mechanism may be still regarded as a physiological mechanism.

In one embodiment, the major mathematical relationship 31 may describe that the second heart rate data 34 of the heart activity is generated to meet the motion data 33 of the external workload determined based on the major physiological mechanism of the human body.

In one embodiment, the major mathematical relationship 31 may describe that the second heart rate data 34 of the heart activity is generated to meet the motion data 33 of the external workload determined based on a physiological requirement in the major physiological mechanism of the human body.

Further based on (A1) the physiological parameter associated with the major physiological mechanism, (B1) the external workload in demand and (C1) the heart activity (e.g., the heart rate) in the paragraph associated with the physiological phenomenon and at least one of Example I and Example II, the major mathematical relationship 31 (i.e., algorithm) in the mathematical model 30 can be set up to comprise: a former relationship between (B1) the motion data 33 and (A1) the value of the physiological parameter associated with the major physiological mechanism of the human body; and a latter relationship between (A1) the value of the physiological parameter associated with the major physiological mechanism of the human body and (C1)

Preferably, the major physiological mechanism of the human body is an aerobic glycolysis (in Example I).

The major physiological mechanism of the human body may be a combination of an aerobic glycolysis for ATP production in the active muscle (in Example I) and an aerobic removal of lactate in the whole body (in Example II). The major physiological mechanism of the human body may be a combination of an aerobic glycolysis for ATP production in the active muscle (in Example I), an aerobic removal of lactate in the whole body (in Example II) and any other minor physiological mechanism.

Figure 5:
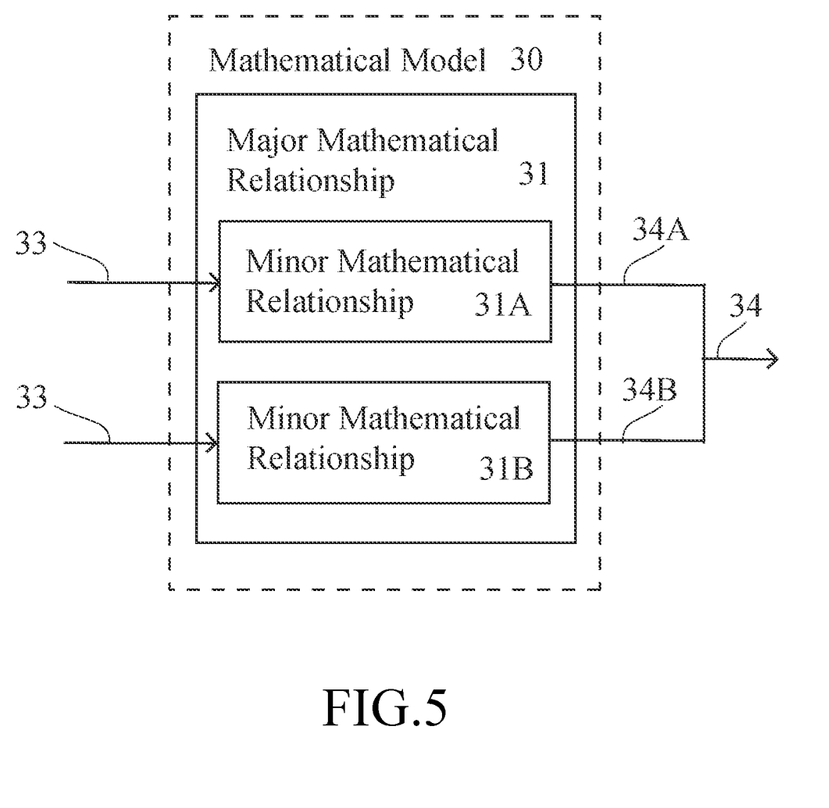
FIG. 5 illustrates one embodiment of the mathematical model in the step 23 in FIG. 2.

FIG. 5 illustrates one embodiment of the mathematical model 30 in the step 23 in FIG. 2. In most cases, the major physiological mechanism of the human body may comprise a plurality of minor physiological mechanisms; the major mathematical relationship 31 may comprise a plurality of minor mathematical relationships 31A, 31B each of which is between the motion data 33 and a portion 34A, 34B of the second heart rate data 34; each of the minor mathematical relationships 31A, 31B is determined based on a minor physiological mechanism of the major physiological mechanism of the human body (It should be noted that the major mathematical relationship 31 only comprises two minor mathematical relationships 31A, 31B in FIG. 5; however, the major mathematical relationship 31 may comprise more than two minor mathematical relationships). In other words, for each of the minor mathematical relationships 31A, 31B, a portion 34A, 34B of the second heart rate data 34 can be calculated based on the motion data 33 in the first duration of the physical activity performed by the user; the heart rate data of each calculated portion 34A, 34B of the second heart rate data 34 has a corresponding value; for each of the minor mathematical relationships 31A, 31B, the corresponding value of the heart rate data of a portion 34A, 34B of the second heart rate data 34 can be calculated based on the motion data 33 in the first duration of the physical activity performed by the user. If the external workload with the motion data 33 is maintained, a portion 34A, 34B of the second heart rate data 34 may increase as the time increases. When the time approaches infinity, a portion 34A, 34B of the second heart rate data 34 may by a constant (see the curve 41 and the curve 42 in FIG. 6).

In one embodiment, the calculated second heart rate data 34 is a sum of the calculated portions 34A, 34B of the second heart rate data 34 (i.e., the minimum value of the heart rate data is inherent and thus isn't taken into account); the value of the heart rate data of the calculated second heart rate data 34 is a sum of the values of the heart rate data of the calculated portions 34A, 34B of the second heart rate data 34. For example: the major mathematical relationship 31 may comprise two minor mathematical relationships: the minor mathematical relationships I (e.g., an aerobic glycolysis for ATP production in the active muscle in Example I) and the minor mathematical relationships II (e.g., an aerobic removal of lactate in the whole body in Example II); the motion data 33 is the speed of 6 km/hr and the second heart rate data 34 calculated based on the speed of 6 km/hr by the major mathematical relationship 31 is the heart rate of 150 BPM; then, a portion of the heart rate of 150 BPM calculated based on the speed of 6 km/hr by the minor mathematical relationship I is 100 BPM and a portion of the heart rate of 150 BPM calculated based on the speed of 6 km/hr by the minor mathematical relationship II is 50BPM. In another embodiment, the calculated second heart rate data 34 is a first sum of the minimum value of the heart rate data and a second sum of the calculated portions 34A, 34B of the second heart rate data 34; the value of the heart rate data of the calculated second heart rate data 34 is the first sum of the minimum value of the heart rate data and the second sum of the values of the heart rate data of the calculated portions 34A, 34B of the second heart rate data 34. For example: the major mathematical relationship 31 may comprise two minor mathematical relationships: the minor mathematical relationships I (e.g., an aerobic glycolysis for ATP production in the active muscle in Example I) and the minor mathematical relationships II (e.g., an aerobic removal of lactate in the whole body in Example II); the motion data 33 is the speed of 6 km/hr and the second heart rate data 34 calculated based on the speed of 6 km/hr by the major mathematical relationship 31 is the heart rate of 150 BPM; then, the minimum value of the heart rate data is the heart rate of 80 BPM, a portion of the heart rate of 150 BPM calculated based on the speed of 6 km/hr by the minor mathematical relationship I is 50 BPM and a portion of the heart rate of 150 BPM calculated based on the speed of 6 km/hr by the minor mathematical relationship II is 20 BPM. For example: the major mathematical relationship 31 may comprise two minor mathematical relationships: the minor mathematical relationships I (e.g., an aerobic glycolysis for ATP production in the active muscle in Example I) and the minor mathematical relationships II (e.g., an aerobic removal of lactate in the whole body in Example II); the motion data 33 is the speed of 6 km/hr and the second heart rate data 34 can be calculated based on the speed of 6 km/hr by the major mathematical relationship 31 is the heart rate reserve of 0.8; then, the minimum value of the heart rate data is the heart rate reserve of 0, a portion of the heart rate reserve of 0.8 calculated based on the speed of 6 km/hr by the minor mathematical relationship I is 0.5 and a portion of the heart rate reserve of 0.8 calculated based on the speed of 6 km/hr by the minor mathematical relationship II is 0.3.

Each calculated portion 34A, 34B of the second heart rate data 34 may have an upper limit value of the heart rate data defined in the corresponding minor mathematical relationship 31A, 31B. The first candidate of the maximum value of the heart rate data may be a third sum of the minimum value of the heart rate data and a fourth sum of the upper limit values of calculated portions 34A, 34B of the second heart rate data 34.

In one embodiment, each of the plurality of minor mathematical relationships 31A, 31B may describe that a portion 34A, 34B of the second heart rate data 34 of the heart activity is generated to meet the motion data 33 of the external workload determined based on the corresponding minor physiological mechanism of the human body.

In one embodiment, each of the plurality of minor mathematical relationships 31A, 31B may describe that a portion 34A, 34B of the second heart rate data 34 of the heart activity is generated to meet the motion data 33 of the external workload determined based on a physiological requirement of the corresponding minor physiological mechanism of the human body.

Further based on (A2) the physiological parameter associated with the minor physiological mechanism, (B2) the external workload in demand and (C2) the heart activity (e.g., the heart rate) in the paragraph associated with the physiological phenomenon and each of Example I and Example II, the minor mathematical relationship 31A, 31B (i.e., algorithm) of the major mathematical relationship 31 in the mathematical model 30 can be set up to comprise: a former relationship between (B2) the motion data 33 and (A2) the value of the physiological parameter associated with the minor physiological mechanism of the human body; and a latter relationship between (A2) the value of the physiological parameter associated with the minor physiological mechanism of the human body and (C2) the portion 34A, 34B of the second heart rate data 34; (C2) the portion 34A, 34B of the second heart rate data 34 of the heart activity is generated to meet (B2) the motion data 33 of the external workload determined based on (A2) the value of the physiological parameter associated with the minor physiological mechanism of the human body. The physiological parameter associated with the minor physiological mechanism of the human body may result from a physiological requirement in the minor physiological mechanism of the human body. The physiological parameter associated with the minor physiological mechanism of the human body may be the physiological parameter required in the minor physiological mechanism of the human body; for example, the physiological parameter associated with the minor physiological mechanism of the human body may be an oxygen supply in each of Example I and Example II; however, the present invention is not limited to this case.

Preferably, one of the minor physiological mechanisms is an aerobic glycolysis (in Example I). More Preferably, two of the minor physiological mechanisms are the aerobic glycolysis (in Example I) and the aerobic removal of lactate (in Example II).

The major mathematical relationship 31 may comprise a first minor mathematical relationship 31A between the motion data 33 and a first portion 34A of the second heart rate data 34 and a second minor mathematical relationship 31B between the motion data 33 and a second portion 34B of the second heart rate data 34; the first minor mathematical relationships 31A may be determined based on a first minor physiological mechanism of the major physiological mechanism of the human body and the second minor mathematical relationships 31B may be determined based on a second minor physiological mechanism of the major physiological mechanism of the human body. Physiologically, the first response speed of the required heart activity in the first minor physiological mechanism may be more than the second response speed of the required heart activity in the second minor physiological mechanism if the same activity intensity is applied in the first minor physiological mechanism and the second minor physiological mechanism. For example, the first minor physiological mechanism is an aerobic glycolysis for ATP production in the active muscle in Example I and the second minor physiological mechanism is an aerobic removal of lactate in the whole body in Example II; however, the present invention is not limited to this case. Correspondingly, the first response speed of the first portion 34A of the second heart rate data 34 in the first minor mathematical relationship 31A may be more than the second response speed of the second portion 34B of the second heart rate data 34 in the second minor mathematical relationship 31B if the same activity intensity is applied in the first minor mathematical relationship 31A and the second minor mathematical relationship 31B, which is also shown in FIG. 6 (i.e., the slope of the curve 41 is more than the slope of the curve 42 in the time interval T).

Figure 6:
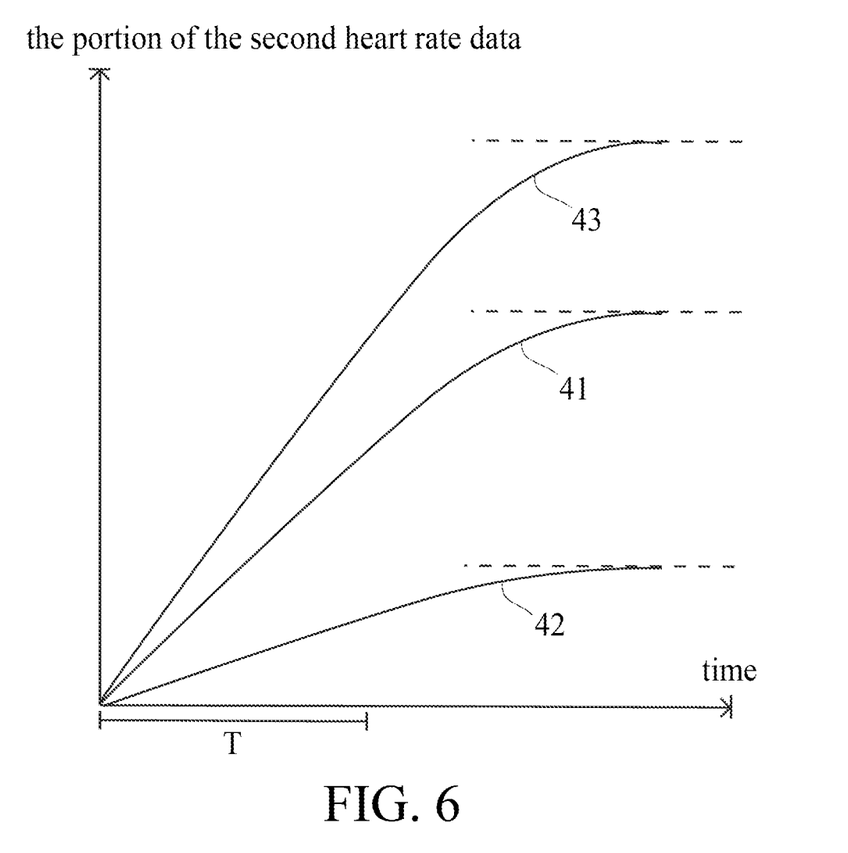
FIG. 6 illustrates that the median curve is derived from the first minor mathematical relationship, the bottom curve is derived from the second minor mathematical relationship and the top curve is derived from the major mathematical relationship if the same activity intensity is applied and maintained in the first minor mathematical relationship, the second minor mathematical relationship and the major mathematical relationship.

FIG. 6 illustrates that the curve 41 is derived from the first minor mathematical relationship 31A, the curve 42 is derived from the second minor mathematical relationship 31B and the curve 43 is derived from the major mathematical relationship 31 (the portion of the second heart rate data 34 is the overall second heart rate data 34 in the curve 43) if the same activity intensity is applied and maintained in the first minor mathematical relationship 31A, the second minor mathematical relationship 31B and the major mathematical relationship 31. The curve 41 represents that the first portion 34A of the second heart rate data 34 varies with time, the curve 42 represents that the second portion 34B of the second heart rate data 34 varies with time and the curve 43 formed by the curve 42 superimposed on the curve 41 represents the second heart rate data 34 varies with time. Each of the first portion 34A of the second heart rate data 34 in the curve 41, the second portion 34B of the second heart rate data 34 in the curve 42 and the second heart rate data 34 in the curve 43 may increase as the time increases. When the time approaches infinity, each of the first portion 34A of the second heart rate data 34 in the curve 41, the second portion 34B of the second heart rate data 34 in the curve 42 and the second heart rate data 34 in the curve 43 may be a constant marked with a dashed line.

Generally, the first minor mathematical relationship 31A has a higher priority in the mathematical model 30 (i.e., algorithm) than the second minor mathematical relationship 31B because of its higher response speed of the portion of the second heart rate data 34. Preferably, the second minor mathematical relationship 31B having the second response speed of the second portion 34B of the second heart rate data 34 less than the first response speed of the first portion 34A of the second heart rate data 34 is appended to the first minor mathematical relationship 31A having the first response speed of the first portion 34A of the second heart rate data 34, which can increase a precision of the estimation of the second heart rate data 34, increase a precision of the comparison C1, C2, . . . , CN between the first heart rate data 32 and the corresponding second heart rate data 34-1, 34-2, 34-N and further increase a precision of the estimation of the maximum value of the heart rate data.

Correspondingly, the first time constant defined in the first minor mathematical relationship 31A may be less than the second time constant defined in the second minor mathematical relationship 31B. Correspondingly, the first portion 34A of the second heart rate data 34 in the first minor physiological mechanism may be more than the second portion 34B of the second heart rate data 34 in the second minor physiological mechanism if the same activity intensity is applied in the first minor mathematical relationship 31A and the second minor mathematical relationship 31B. For example: the major mathematical relationship 31 may comprise two minor mathematical relationships: the minor mathematical relationships I (an aerobic glycolysis for ATP production in the active muscle in Example I) and the minor mathematical relationships II (an aerobic removal of lactate in the whole body in Example II); the motion data 33 is the speed of 6 km/hr and the second heart rate data 34 calculated based on the speed of 6 km/hr by the major mathematical relationship 31 is the heart rate of 150 BPM; then, a portion of the heart rate of 150 BPM calculated based on the speed of 6 km/hr by the minor mathematical relationship I is 100 BPM and a portion of the heart rate of 150 BPM calculated based on the speed of 6 km/hr by the minor mathematical relationship II is 50BPM.

Physiologically, the first threshold of the activity intensity (e.g., exercise intensity) above which the first minor physiological mechanism is expressed may be less than the second threshold of the activity intensity above which the second minor physiological mechanism is expressed. For example, the first minor physiological mechanism may be an aerobic glycolysis for ATP production in the active muscle in Example I and the second minor physiological mechanism may be an aerobic removal of lactate in the whole body in Example II; however, the present invention is not limited to this case. Correspondingly, the first threshold of the activity intensity (e.g., exercise intensity) above which the first minor mathematical relationship 31A is operated may be less than the second threshold of the activity intensity above which the second minor mathematical relationship 31B is operated, which is also shown in FIG. 7A and FIG. 7B.

Figure 7A:
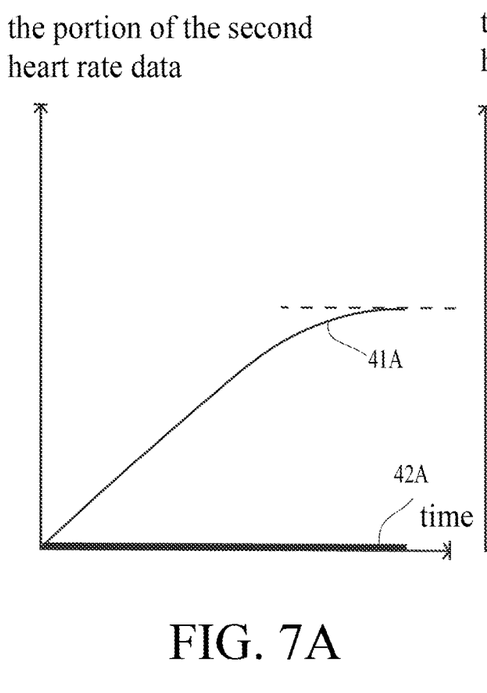
FIG. 7A illustrates that the top curve is derived from the first minor mathematical relationship, the zero level is derived from the second minor mathematical relationship when the same activity intensity between the first threshold and the second threshold is applied and maintained in the first minor mathematical relationship and the second minor mathematical relationship.
Figure 7B:
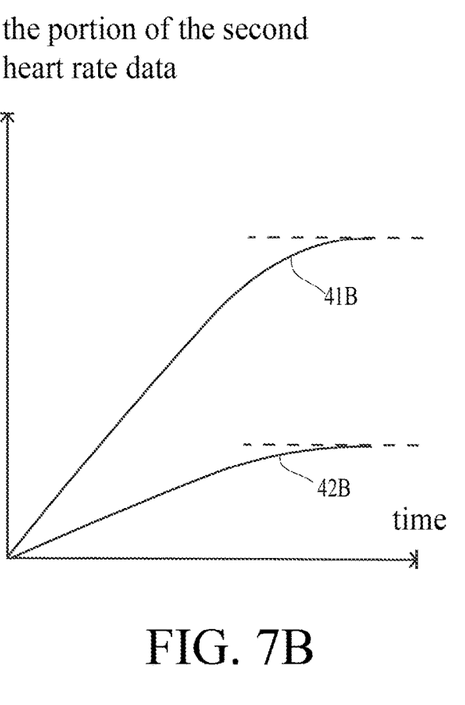
FIG. 7B illustrates that the top curve is derived from the first minor mathematical relationship, the bottom curve is derived from the second minor mathematical relationship when the same activity intensity more than the second threshold is applied and maintained in the first minor mathematical relationship and the second minor mathematical relationship.

FIG. 7A illustrates that the curve 41A is derived from the first minor mathematical relationship 31A, the zero level 42A is derived from the second minor mathematical relationship 31B when the same activity intensity (e.g., exercise intensity) between the first threshold and the second threshold is applied and maintained in the first minor mathematical relationship 31A and the second minor mathematical relationship 31B. The curve 41A represents that the first portion 34A of the second heart rate data 34 varies with time and the zero level 42A represents that the second portion 34B of the second heart rate data 34 is maintained to be zero. FIG. 7B illustrates that the curve 41B is derived from the first minor mathematical relationship 31A, the curve 42B is derived from the second minor mathematical relationship 31B when the same activity intensity more than the second threshold is applied and maintained in the first minor mathematical relationship 31A and the second minor mathematical relationship 31B. The curve 41B represents that the first portion 34A of the second heart rate data 34 varies with time and the curve 42B represents that second portion 34B of the second heart rate data 34 varies with time. Each of the first portion 34A of the second heart rate data 34 in the curve 41A, the first portion 34A of the second heart rate data 34 in the curve 41B and the second portion 34B of the second heart rate data 34 in the curve 42B may increase as the time increases. When the time approaches infinity, each of the first portion 34A of the second heart rate data 34 in the curve 41A, the first portion 34A of the second heart rate data 34 in the curve 41B and the second portion 34B of the second heart rate data 34 in the curve 42B may be a constant marked with a dashed line.

Generally, the first minor mathematical relationship 31A has a higher priority in mathematical model 30 (i.e., algorithm) than the second minor mathematical relationship 31B because its lower operated threshold of the activity intensity (above which the first minor mathematical relationship 31A is operated). Preferably, the second minor mathematical relationship 31B having the second operated threshold of the activity intensity (above which the second minor mathematical relationship 31B operated) more than the first operated threshold of the activity intensity (above which the first minor mathematical relationship 31A is operated) is appended to the first minor mathematical relationship 31A having the first operated threshold of the activity intensity (above which the first minor mathematical relationship 31A is operated), which can increase a precision of the estimation of the second heart rate data 34, increase a precision of the comparison C1, C2, CN between the first heart rate data 32 and the corresponding second heart rate data 34-1, 34-2, . . . , 34-N and further increase a precision of the estimation of the maximum value of the heart rate data.

Major/Minor Mathematical Relationship (e.g., algorithm) in the Mathematical Model Determined Based on Example I of the Physiological Phenomenon:

Because the response speed of the required heart activity in Example I of the Physiological Phenomenon is relatively high, the parameter of the heart activity in the steady state can be also regarded as be the physiological parameter associated with the physiological mechanism of the human body. The parameter of the heart activity in the steady state is the first parameter of the second heart rate data 34 or a portion 34A, 34B of the second heart rate data 34 symbolized as S. The external workload uses the parameter of motion data symbolized as P. The heart activity uses the second parameter of the second heart rate data 34 or a portion 34A, 34B of the second heart rate data 34 symbolized as Hs. The following formula is an example of the former relationship between S and P:

$$S(P) = H_{Smax} \times 2\left(\frac{1}{1+e^{-\frac{P}{u}}} - 0.5\right)$$

where $H_{Smax}$ is the maximum of the second heart rate data 34 or a portion 34A, 34B of the second heart activity 34 and u is a coefficient adjusted according to the observation of the physiological phenomenon. The following formula is an example of the latter relationship between Hs and S:

$$\frac{\partial H_s(P, t)}{\partial t} = \frac{S(P) - H_s(P, t)}{\tau_1}$$

where $\tau_1$ is the time constant corresponding to Example I of the Physiological Phenomenon and $\tau$ is time.

Major/Minor Mathematical Relationship (e.g., algorithm) in the Mathematical Model Determined Based on Example II of the Physiological Phenomenon:

The physiological parameter associated with the physiological mechanism of the human body is the oxygen supply in aerobic removal of lactate in the whole body symbolized as L. L increases as lactate increases. The external workload uses the parameter of motion data symbolized as P. The heart activity uses the parameter of the second heart rate data 34 or a portion 34A, 34B of the second heart rate data 34 symbolized as $H_L$. The following formula is an example of the former relationship between L and P:

$$\frac{\partial L(L, P, t)}{\partial t} = p_0 + \frac{f_1(L, P)}{\tau_2} - \frac{f_2(L, P)}{\tau_3}$$

where $f_1(L, P)$ is production of lactate associated with anaerobic glycolysis, $f_2(L, P)$ is removal of lactate associated with lactate used to produce ATP or the chemical reaction rate depending on the lactate concentration, $\tau_2$ is the time constant corresponding to production of lactate, $\tau_3$ is the time constant corresponding to removal of lactate, $p_o$ is a coefficient adjusted according to the observation of the physiological phenomenon and t is time. The following formula is an example of the latter relationship between $H_L$ and L:

$$H_L(L) = H_{Lmax} \times \left(1 - m \times e^{-\frac{L}{n}}\right)$$

where $H_{Lmax}$ is the maximum of the second heart rate data 34 or a portion 34A, 34B of the second heart activity 34 and m, n are coefficients adjusted according to the observation of the physiological phenomenon.

The above disclosure is related to the detailed technical contents and inventive features thereof. People skilled in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for determining a maximum value of a heart rate data of a user performing a physical activity, the method comprising:
   acquiring, by a heart rate sensor, first heart rate data in a first duration of the physical activity performed by the user;
   acquiring, by a motion sensor, motion data in the first duration of the physical activity performed by the user;
   providing, by a processor, a plurality of candidates of the maximum value of the heart rate data;
   for each first candidate of the plurality of candidates of the maximum value of the heart rate data, performing, by a processor, a process comprising steps of:
     calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by the first candidate of the maximum value of the heart rate data defined in the major mathematical relationship;

wherein the major mathematical relationship comprises:
a former relationship between the motion data and a value of a physiological parameter associated with the major physiological mechanism of the human body; and
a latter relationship between the value of the physiological parameter associated with the major physiological mechanism of the human body and the second heart rate data;
wherein the second heart rate data of a heart activity is generated to meet the motion data of an external workload determined based on the value of the physiological parameter associated with the major physiological mechanism of the human body;
wherein the major physiological mechanism is a mechanism of an aerobic glycolysis for ATP production in active muscles;
wherein the physiological parameter is an oxygen supply in the aerobic glycolysis for ATP production in the active muscles associated with the major physiological mechanism of the aerobic glycolysis for ATP production in the active muscles, and
making a comparison between the first heart rate data and the second heart rate data; and
choosing, by the processor, one first candidate of the plurality of candidates of the maximum value of the heart rate data as an estimation of the maximum value of the heart rate data of the user based on each comparison between the first heart rate data and the second heart rate data;
wherein the first candidate with a minimum difference between the first heart rate data and the second heart rate data is chosen as the estimation of the maximum value of the heart rate data.

2. The method according to claim 1, wherein under the major mathematical relationship, the second heart rate data of a heart activity is generated to meet the motion data of the external workload determined based on the major physiological mechanism of the human body.

3. The method according to claim 1, wherein under the major mathematical relationship, the second heart rate data of a heart activity is generated to meet the motion data of the external workload determined based on a physiological requirement in the major physiological mechanism of the human body.

4. The method according to claim 1, wherein the physiological parameter associated with the major physiological mechanism of the human body results from a physiological requirement in the major physiological mechanism of the human body.

5. The method according to claim 1, wherein the physiological parameter associated with the major physiological mechanism of the human body is the physiological parameter required in the major physiological mechanism of the human body.

6. The method according to claim 1, wherein the physical activity is an exercise.

7. The method according to claim 1, wherein the major mathematical relationship further comprises a plurality of minor mathematical relationships, each of which is between the motion data and a portion of the second heart rate data, wherein each of the plurality of minor mathematical relationships is determined based on a minor physiological mechanism of the major physiological mechanism of the human body; wherein, each of the minor physiological mechanisms is another mechanism of the aerobic glycolysis for ATP production in the active muscles.

8. The method according to claim 7, wherein under each of the plurality of minor mathematical relationships, the portion of the second heart rate data of a heart activity is generated to meet the motion data of the external workload determined based on the minor physiological mechanism of the human body.

9. The method according to claim 7, wherein under each of the plurality of minor mathematical relationships, the portion of the second heart rate data of a heart activity is generated to meet the motion data of the external workload determined based on a physiological requirement of the minor physiological mechanism of the human body.

10. The method according to claim 7, wherein each of the plurality of minor mathematical relationships comprises:
a former relationship between the motion data and a value of a physiological parameter associated with the minor physiological mechanism of the human body; and
a latter relationship between the value of the physiological parameter associated with the minor physiological mechanism of the human body and the portion of the second heart rate data;
wherein the portion of the second heart rate data of the heart activity is generated to meet the motion data of the external workload determined based on the value of the physiological parameter associated with the minor physiological mechanism.

11. The method according to claim 7, wherein the calculated second heart rate data is a first sum of the minimum value of the heart rate data and a second sum of the calculated portions of the second heart rate data.

12. The method according to claim 11, wherein each of the calculated portions of the second heart rate data has an upper limit value of the heart rate data defined in the corresponding minor mathematical relationship.

13. The method according to claim 12, wherein the first candidate of the maximum value of the heart rate data is a third sum of the minimum value of the heart rate data and a fourth sum of the upper limit values of the calculated portions of the second heart rate data.

14. A method for determining a maximum value of a heart rate data of a user performing a physical activity, the method comprising:
acquiring, by a heart rate sensor, first heart rate data in a first duration of the physical activity performed by the user;
acquiring, by a motion sensor, motion data in the first duration of the physical activity performed by the user;
providing a plurality of candidates of the maximum value of the heart rate data;
for each first candidate of the plurality of candidates of the maximum value of the heart rate data, performing, by a processor, a process comprising steps of:
calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by a minimum value of the heart rate data and the first candidate of the maximum value of the heart rate data defined in the major mathematical relationship; and making a comparison between the first heart rate data and the second heart rate data; and choosing, by the processor, one first candidate of the plurality of candidates of the maximum value of the heart rate data as an estimation of the maximum value of the heart rate data of the user based on each comparison between the first heart rate data and the second heart rate data;

wherein the major mathematical relationship comprises a first minor mathematical relationship between the motion data and a first portion of the second heart rate data and a second minor mathematical relationship between the motion data and a second portion of the second heart rate data, wherein the first minor mathematical relationship is determined based on a first minor physiological mechanism of the major physiological mechanism of the human body and the second minor mathematical relationship is determined based on a second minor physiological mechanism of the major physiological mechanism of the human body, wherein a first response speed of the first portion of the second heart rate data in the first minor mathematical relationship is more than a second response speed of the second portion of the second heart rate data in the second minor mathematical relationship if the same activity intensity is applied in the first minor mathematical relationship and the second minor mathematical relationship;

wherein the major mathematical relationship, the first minor mathematical relationship, and the second minor mathematical relationship respectively comprises:
a former relationship between the motion data and a value of a physiological parameter associated with the major physiological mechanism of the human body; and
a latter relationship between the value of the physiological parameter associated with the major physiological mechanism of the human body and the second heart rate data;
wherein the second heart rate data of a heart activity is generated to meet the motion data of an external workload determined based on the value of the physiological parameter associated with the major physiological mechanism of the human body;

wherein the major physiological mechanism, the first minor physiological mechanism, and the second minor physiological mechanism are different mechanisms of an aerobic glycolysis for ATP production in active muscles;

wherein the physiological parameter is an oxygen supply in the aerobic glycolysis for ATP production in the active muscles associated with the major physiological mechanism of the aerobic glycolysis for ATP production in the active muscles;

wherein the first candidate with a minimum difference between the first heart rate data and the second heart rate data is chosen as the estimation of the maximum value of the heart rate data.

15. A method for determining a maximum value of a heart rate data of a user performing a physical activity, the method comprising:
acquiring, by a heart rate sensor, first heart rate data in a first duration of the physical activity performed by the user;
acquiring, by a motion sensor, motion data in the first duration of the physical activity performed by the user;
providing a plurality of candidates of the maximum value of the heart rate data;
for each first candidate of the plurality of candidates of the maximum value of the heart rate data, performing, by a processor, a process comprising steps of:
calculating second heart rate data based on the motion data in the first duration of the physical activity performed by the user by a mathematical model comprising a major mathematical relationship between the motion data and the second heart rate data, wherein the major mathematical relationship is determined based on a major physiological mechanism of a human body, wherein the calculated second heart rate data is constrained by a minimum value of the heart rate data and the first candidate of the maximum value of the heart rate data defined in the major mathematical relationship; and
making a comparison between the first heart rate data and the second heart rate data; and
choosing, by the processor, one first candidate of the plurality of candidates of the maximum value of the heart rate data as an estimation of the maximum value of the heart rate data of the user based on each comparison between the first heart rate data and the second heart rate data;

wherein the major mathematical relationship comprises a first minor mathematical relationship between the motion data and a first portion of the second heart rate data and a second minor mathematical relationship between the motion data and a second portion of the second heart rate data, wherein the first minor mathematical relationship is determined based on a first minor physiological mechanism of the major physiological mechanism of the human body and the second minor mathematical relationship is determined based on a second minor physiological mechanism of the major physiological mechanism of the human body, wherein a first threshold of an activity intensity above which the first minor mathematical relationship is operated is less than a second threshold of the activity intensity above which the second minor mathematical relationship is operated;

wherein the major mathematical relationship, the first minor mathematical relationship, and the second minor mathematical relationship respectively comprises:
a former relationship between the motion data and a value of a physiological parameter associated with the major physiological mechanism of the human body; and
a latter relationship between the value of the physiological parameter associated with the major physiological mechanism of the human body and the second heart rate data;
wherein the second heart rate data of a heart activity is generated to meet the motion data of an external workload determined based on the value of the physiological parameter associated with the major physiological mechanism of the human body;

wherein the major physiological mechanism, the first minor physiological mechanism, and the second minor physiological mechanism are different mechanisms of an aerobic glycolysis for ATP production in the active muscles;

wherein the physiological parameter is an oxygen supply in the aerobic glycolysis for ATP production in the active muscles associated with the major physiological mechanism of the aerobic glycolysis for ATP production in the active muscles;

wherein the first candidate with a minimum difference between the first heart rate data and the second heart rate data is chosen as the estimation of the maximum value of the heart rate data.

\* \* \* \* \*